US00PP12753P2

(12) United States Plant Patent
Westhoff

(10) Patent No.: US PP12,753 P2
(45) Date of Patent: Jul. 2, 2002

(54) CALIBRACHOA PLANT NAMED 'WESCACHERRY'

(75) Inventor: Heinrich Westhoff, Sudlohn-Oeding (DE)

(73) Assignee: Josef & Heinrich Westhoff Gartenbau-Spezialkulteren, Südlohn-Oeding (DE)

( * ) Notice: Subject to any disclaimer, the term of this patent is extended or adjusted under 35 U.S.C. 154(b) by 1 days.

(21) Appl. No.: 09/797,251

(22) Filed: Mar. 1, 2001

(51) Int. Cl.[7] ..... A01H 5/00
(52) U.S. Cl. ..... Plt./263
(58) Field of Search ..... Plt./263, 356

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Calibrachoa plant named 'Wescacherry', characterized by its upright to semi-upright growth habit; large flower size; intense purple red-colored flowers; flowers that do not close with low light levels or at night; and good weather tolerance.

1 Drawing Sheet

BACKGROUND OF THE INVENTION

The present Invention relates to a new and distinct cultivar of Calibrachoa plant, botanically known as *Calibrachoa hybrida*, and hereinafter referred to by the name 'Wescacherry'.

The new Calibrachoa is a product of a planned breeding program conducted by the Inventor in Sudlohn-Oeding, Germany. The new Calibrachoa originated from a cross made by the Inventor of a proprietary selection of Calibrachoa identified as code number 97-116, not patented, as the female, or seed, parent with a proprietary selection of Calibrachoa identified as code number 98-120, not patented, as the male, or pollen, parent. The new Calibrachoa was selected by the Inventor in 1999 on the basis of its large flower size. Plants of the new Calibrachoa differ from plants of the parent selections primarily in flower color and flower size.

Asexual reproduction of the new cultivar by terminal cuttings taken at Sudlohn-Oeding, Germany, has shown that the unique features of this new Calibrachoa are stable and reproduced true to type in successive generations.

SUMMARY OF THE INVENTION

Plants of the cultivar Wescacherry have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Wescacherry'. These characteristics in combination distinguish 'Wescacherry' as a new and distinct cultivar:

1. Upright to semi-upright growth habit.
2. Large flower size.
3. Intense purple red-colored flowers.
4. Flowers that do not close with low light levels or at night.
5. Good weather tolerance.

Plants of the cultivar Wescacherry can be compared to plants of the Calibrachoa cultivar Million Bells Cherry, not patented. However in side-by-side comparisons conducted by the Inventor in Sudlohn-Oeding, Germany, plants of the new Calibrachoa and the cultivar Million Bells Cherry differ in the following characteristics:

1. Plants of the new Calibrachoa have larger flowers than plants of the cultivar Million Bells Cherry.
2. Flower throat color of plants of the new Calibrachoa is more intense yellow than flower throat color of plants of the cultivar Million Bells Cherry.
3. Leaves of the new Calibrachoa are darker green than leaves of the cultivar Million Bells Cherry.
4. Plants of the new Calibrachoa are more upright and have stronger lateral branches than plants of the cultivar Million Bells Cherry.

Plants of the cultivar Wescacherry can also be compared to plants of the pink-flowered Calibrachoa cultivar Wespink, disclosed in U.S. Plant Patent Ser. No. 09/592,377. However in side-by-side comparisons conducted by the Inventor in Sudlohn-Oeding, Germany, plants of the new Calibrachoa and the cultivar Wespink differ in the following characteristics:

1. Plants of the new Calibrachoa have larger flowers and larger leaves than plants of the cultivar Wespink.
2. Plants of the new Calibrachoa are more upright than plants of the cultivar Wespink.
3. Plants of the new Calibrachoa have stronger lateral branches than plants of the cultivar Wespink.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Calibrachoa. The photograph comprises a side perspective view of a typical plant of 'Wescacherry'.

DETAILED BOTANICAL DESCRIPTION

In the following description, color references are made to The Royal Horticultural Society Colour Chart, 1995 edition, except where general terms of ordinary dictionary significance are used. Plants grown in containers were used for following description. Plants were grown under conditions which closely approximate commercial production conditions during the spring in Sudlohn-Oeding, Germany. Plants used for the description and the photographs were about 10 to 12 weeks from planting rooted cuttings.

Botanical classification: *Calibrachoa hybrida* cultivar Wescacherry.

Parentage:

*Female parent.*—Proprietary selection of *Calibrachoa hybrida* identified as 97-116, not patented.

*Male parent.*—Proprietary selection of *Calibrachoa hybrida* identified as 98-120, not patented.

Propagation:

*Type cutting.*—Terminal vegetative cuttings.

*Time to initiate roots.*—About two to three weeks at 20° C.

*Time to develop roots.*—About three to four weeks at 20° C.

*Root description.*—Numerous, fine, fibrous, and well-branched.

Plant description:

*Form.*—Annual flowering plant; initially upright to semi-upright; uniform, rounded appearance, plants eventually become spherical in overall shape. Pinching enhances branching at every node.

*Usage.*—Appropriate for hanging baskets, window boxes and patio containers.

*Plant height* (*from soil level to top of plant plane*).—About 28 cm.

*Plant length* (*from soil level to lateral branches apices*).—About 57 cm.

*Plant diameter* (*area of spread*).—About 50 cm.

*Stem description.*—Main branches, length: About 57 cm. Main branches, diameter: About 3.75 mm. Main branches, internode length: About 2.7 cm. Lateral branches, length: About 15 to 20 cm. Lateral branches, diameter: About 2 mm. Lateral branches, internode length: About 2 cm. Texture: Dense white pubescence. Strength: Strong, wiry. Color: 146C with slight anthocyanin, 166A to 166B.

*Foliage description.*—Leaves simple, generally symmetrical and long persisting; sessile. Arrangement: Alternate. Length: About 3.6 cm. Width: About 1.3 cm. Shape: Elliptic. Apex: Obtuse, rounded. Base: Attenuate. Margin: Entire. Aspect: Mostly flat. Texture: Sparse white pubescence. Color: Young foliage, upper surface: 147A. Young foliage, lower surface: 147B. Mature foliage, upper surface: 147A; veins, 147B. Mature foliage, lower surface: 147C, veins, 147C.

Flower description:

*Flower type and habit.*—Large-sized flowers; flowers face upright or outward; single, axillary. Flowers persistent. Freely flowering.

*Natural flowering season.*—Spring until frost in the autumn; flowering continuous.

*Flower longevity on the plant.*—About one week.

*Flower size.*—Diameter: About 3.5 cm. Depth (height): About 2.2 cm. Tube length: About 2.1 cm. Throat diameter, distal end: About 9 mm. Tube diameter, proximal end: About 3 mm.

*Flower buds* (*just showing color*).—Length: About 2.5 cm. Diameter: About 5 mm. Shape: Oblong. Color: Apex, 187D; mid-section, 187A; base, 17D, veins, 187A.

*Corolla.*—Arrangement/appearance: Single whorl of five petals, fused into flared trumpet. Petal length from throat: About 1.5 cm. Petal width: About 1.6 cm. Petal shape: Roughly spatulate with obtuse apex with cuspidate tendencies. Petal margin: Entire. Petal texture: Smooth, satiny. Color: Petal, upper surface, when opening: 60A. Petal, lower surface, when opening: 60B. Petal, upper surface, opened flower: 61B, fading to 74A; veins, 59A or 60A to 60B. Petal, lower surface, opened flower: 61B; veins, 187A. Flower throat (inside): 17A; veins, 187A. Flower eye or ring, about 3 to 5 mm in diameter at top of throat: 59A to 60A. Flower tube (outside): 13B; veins, 187A or 166A.

*Sepals.*—Arrangement/appearance: Single whorl of five sepals, star-shaped. Length: About 2 cm. Width: About 3.6 cm. Shape: Lanceolate. Apex: Rounded. Margin: Entire. Texture: Dense white pubescence. Color: Upper surface: 147A. Lower surface: 147B.

*Peduncles.*—Length: About 1.75 cm. Width: About 1 mm. Strength: Flexible and wiry, flowers held upright or outward. Color: 144A with anthocyanin, 187A, towards the sepals.

*Reproductive organs.*—Stamens: Quantity per flower: 5. Filament color: Close to 144B. Anther shape: Four-parted, oval. Anther length: About 2 mm. Anther color: 11A. Pollen amount: Moderate. Pollen color: 11A. Pistils: Quantity per flower: 1. Pistil length: About 1.25 cm. Stigma shape: Oval. Stigma color: Immature: 146D. Mature: 146C. Style length: About 1.1 cm. Style color: 145B to 145C. Ovary color: 145A.

*Seed.*—Seed production has not been observed.

Disease resistance: Plants of the new Calibrachoa have not been noted to be resistant to pathogens common to Calibrachoa.

Weather tolerance: Plants of the new Calibrachoa are tolerant to rain and wind.

It is claimed:

1. A new and distinct cultivar of Calibrachoa plant named 'Wescacherry', as illustrated and described.

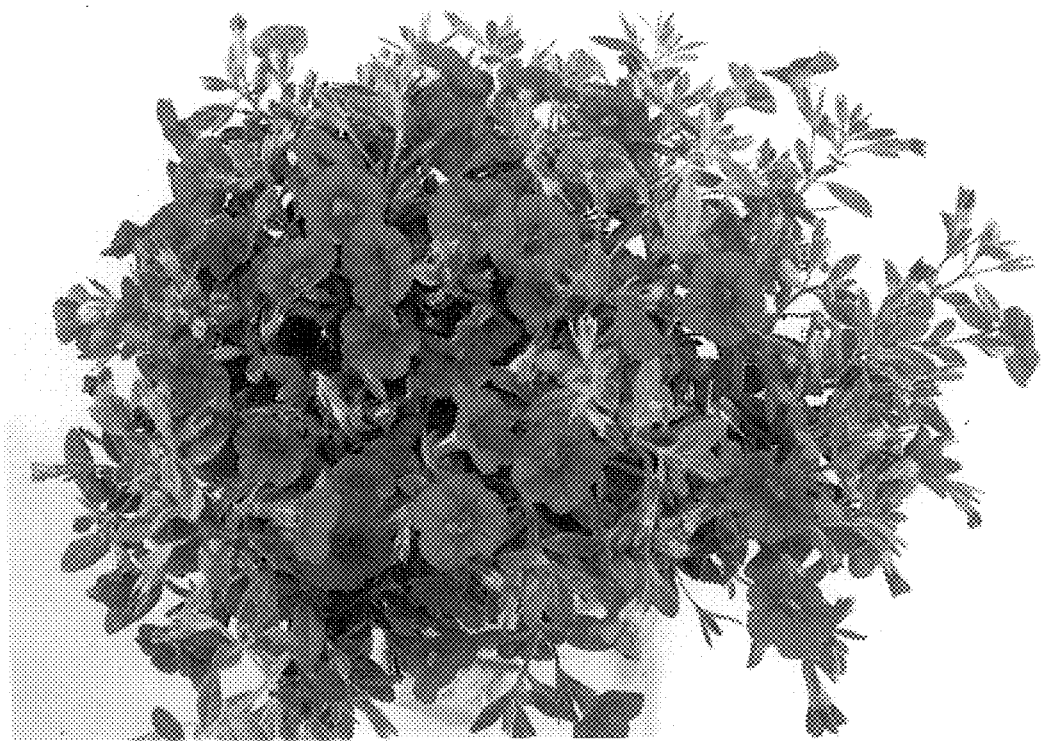

* * * * *